US008759079B2

(12) United States Patent
Kwon

(10) Patent No.: US 8,759,079 B2
(45) Date of Patent: Jun. 24, 2014

(54) DEVICE FOR AUTOMATICALLY ANALYZING NUCLEIC ACID

(75) Inventor: Oh Won Kwon, Daejeon (KR)

(73) Assignee: Korea Institute of Machinery & Materials, Daejeon (KR)

( * ) Notice: Subject to any disclaimer, the term of this patent is extended or adjusted under 35 U.S.C. 154(b) by 0 days.

(21) Appl. No.: 13/314,571

(22) Filed: Dec. 8, 2011

(65) Prior Publication Data

US 2013/0122576 A1 May 16, 2013

(30) Foreign Application Priority Data

Nov. 15, 2011 (KR) ........................ 10-2011-0119036

(51) Int. Cl.

*C12M 1/00* (2006.01)
*C12M 1/36* (2006.01)
*C12M 1/38* (2006.01)
*C12M 1/34* (2006.01)
*C12M 3/00* (2006.01)

(52) U.S. Cl.

USPC .................. 435/287.2; 435/283.1; 435/287.1; 435/286.4; 435/286.7; 435/287.4

(58) Field of Classification Search

USPC ........................................... 435/283.1–309.4
See application file for complete search history.

(56) References Cited

U.S. PATENT DOCUMENTS

| | | | | |
|---|---|---|---|---|
| 5,882,903 | A | 3/1999 | Andrevski | |
| 6,432,694 | B1 * | 8/2002 | Malmqvist | 435/286.5 |
| 6,706,519 | B1 * | 3/2004 | Kellogg et al. | 435/287.2 |
| 7,462,323 | B1 | 12/2008 | Chang | |
| 7,727,473 | B2 | 6/2010 | Ching | |
| 7,754,148 | B2 | 7/2010 | Yu | |
| 7,910,062 | B2 | 3/2011 | Yu | |
| 2005/0244837 | A1 * | 11/2005 | McMillan | 435/6 |
| 2006/0011539 | A1 | 1/2006 | Lee | |
| 2006/0177844 | A1 | 8/2006 | Ching | |
| 2008/0003588 | A1 | 1/2008 | Hasson | |
| 2008/0057572 | A1 | 3/2008 | Petersen | |
| 2009/0148933 | A1 * | 6/2009 | Battrell et al. | 435/287.2 |
| 2010/0279392 | A1 | 11/2010 | Kodama | |
| 2011/0030809 | A1 | 2/2011 | Ying | |
| 2011/0158849 | A1 | 6/2011 | Yu | |

FOREIGN PATENT DOCUMENTS

| | | |
|---|---|---|
| CN | 1717280 | 1/2006 |
| CN | 101802163 | 8/2010 |
| KR | 10-2011-0108857 | 1/1997 |
| KR | 10-2008-0071995 | 8/2008 |
| KR | 10-2010-0103460 | 10/2008 |
| WO | 2007-047814 | 4/2007 |

(Continued)

OTHER PUBLICATIONS

Guolin Xu et el., A self-contained polymeric cartridge for automated biological sample preparation, Institute of Bioengineering and Nanotechnology, Jul. 25, 2011.

*Primary Examiner* — Nathan Bowers
*Assistant Examiner* — Lydia Edwards
(74) *Attorney, Agent, or Firm* — Lexyoume IP Meister, PLLC

(57) ABSTRACT

An apparatus for automatically analyzing a nucleic acid includes: a sample preprocessing device including a plurality of chambers in which reagents mixed with a sample are accommodated according to sample preprocessing process order for extracting a nucleic acid from the sample; and a nucleic amplifying and detecting device connected with the sample preprocessing device to receive the nucleic acid extracted from the sample.

15 Claims, 8 Drawing Sheets

(56) References Cited

FOREIGN PATENT DOCUMENTS

| | | |
|---|---|---|
| WO | 2011019428 | 2/2011 |
| WO | 2011/054353 | 5/2011 |
| WO | 97-02357 | 10/2011 |

* cited by examiner

DEVICE FOR AUTOMATICALLY ANALYZING NUCLEIC ACID

CROSS-REFERENCE TO RELATED APPLICATION

This application claims priority to and the benefit of Korean Patent Application No. 10-2011-0119036 filed in the Korean Intellectual Property Office on Nov. 15, 2011, the entire contents of which are incorporated herein by reference.

BACKGROUND OF THE INVENTION (a) Field of the Invention

The present invention relates to an apparatus for automatically analyzing a nucleic acid and, more specifically, to an apparatus for automatically analyzing a nucleic acid capable of simplifying sample preprocessing and deoxyribonucleic acid (DNA) and ribonucleic acid (RNA) amplifying and detecting processes.

(b) Description of the Related Art

In general, molecular diagnosis, which measures DNA, RNA, protein, or metabolite to capture genotype or measure gene variances, biochemical changes, or the like, of a human body, is a sector growing on the back of development of devices for analyzing and determining Omics (i.e., sciences recognizing an organism (or a living thing) as a network and investigating interactions between constituents of the overall novel network behaviors, and the like) and informatics technologies.

As for growth factors over demands, the growth of molecular diagnosis is promoted by various factors such as an increase in demand for customized medical treatment to minimize high clinical failure rates, low patient suitability of developed new medicine, and side effects and to rationalize, medicine costs through reduction of high bio-medical costs, and the like.

However, in the aspect that molecular diagnosis is a tool or means for accurate decision making, reliability, accuracy, rapidness, and convenience have been discussed as the most critical issues, and in particular, a considerable level of technological development is required in various fields such as a device for integrating bio-information and clinical medicine information to create useful knowledge and applying the same, or the like.

In the aspect of business, overcoming low interest in investment, high level of dependency on major medicine development enterprises, an issue including compensation, development of various models available for a direct service to patients, and the like, have been raised as major tasks.

Meanwhile, a molecular diagnosis inspection undergoes a sample preprocessing process of extracting a nucleic acid, or the like, form a specimen such as a blood sample, or the like. A polymerase chain reaction (PCR) of the sample preprocessing process is a very well known DNA replication method. The use of the technique can selectively and, quickly mass-replicate any DNAs, so PCR is essentially used in various genetic fields such as diagnosing and treating hereditary diseases, forensic medicine, and the like. With this method, DNA desired to be replicated is repeatedly replicated in respective replication steps, each having a particular reaction temperature, by using a DNA polymerase.

Such a replication process uses a periodical circulation of a thermally controlled reaction process, and the amount of initial start molecules is increased as the temperature circulation process is repeated. In general, a DNA replication process through PCR is executed through a replication process by stage.

Namely, PCR starts with a double-strand DNA, and a first reaction of each circulation period is separating the two strands through a heat treatment, which is called denaturing and generally executed at 95° C. The next is a cooling process of coupling primers (a gene sequence of a short single line complementary to a particular gene sequence and synthesized for the purpose of being used in PCR diagnosis, a DNA base sequence determination method, or the like) to the two separated DNA strands. This process is called annealing and executed at 40 to 65° C. A final step is a polymerization process in which a DNA polymerase in the mixture starts DNA synthesis starting from the primers. This process is called extension and executed at 70° C. to 75° C. Here, an accurate temperature of each step may be different according to diagnosis inspection items.

Performing the foregoing sample preprocessing process including a process of mixing a sample and a reagent and, a process of processing a residual consumes a lot of time. In addition, the existing device for performing the sample processing process is fabricated to have a complicating structure, increasing the fabrication unit cost and consumption goods, and when a large amount of samples are collectively processed, the samples may be contaminated.

The above information disclosed in this Background section is only for the enhancement of understanding of the background of the invention and therefore it may contain information that does not form the prior art that is already known in this country to a person of ordinary skill in the art.

SUMMARY OF THE INVENTION

The present invention has been made in an effort to provide an apparatus for automatically analyzing a nucleic acid including a sample preprocessing device capable of simplifying a process of preprocessing a sample and a nucleic acid amplifying and detecting device capable of simplifying a process of amplifying and detecting a nucleic acid.

An exemplary embodiment of the present invention provides an apparatus for automatically analyzing a nucleic acid including: a sample preprocessing device including a plurality of chambers in which reagents mixed with a sample are accommodated according to sample preprocessing process order for extracting a nucleic acid from the sample; and a nucleic amplifying and detecting device connected with the sample preprocessing device to receive the nucleic acid extracted from the sample.

The sample preprocessing device may further include a mixing unit coupled to a lower portion of the chamber, receiving a reagent discharged from an opened lower portion of the chamber, and mixing the reagent and the sample.

The mixing unit may include a baffle installed on the bottom thereof.

The chamber may include a nozzle through which air is supplied, and the lower portion of the chamber may be opened and closed according to a change in an internal pressure of the chamber by air supplied through the nozzle.

The lower portion of the chamber may be made of an elastic film, and when the internal pressure of the chamber is increased by air supplied through the nozzle, the elastic film elongates to open the lower portion of the chamber.

The elastic film may be made of one of an elastic film or elastic plastic.

The mixing unit may include an inlet pipe through which the sample is introduced. The chambers may be installed to be contiguous along an outer surface of the inlet pipe.

The apparatus may further include a collecting unit coupled to a lower portion of the mixing unit and collecting an effluent in which the sample and the reagent are mixed.

The apparatus may further include a magnet bar coupled to one side of the collecting unit collecting DNA extracted from the sample.

The apparatus may further include a residual discharge check valve coupled to a lower portion of the collecting unit to allow a residual to be discharged therethrough, and an effluent discharge check valve allowing the effluent finally collected from the sample preprocessing device to be discharged therethrough, wherein the effluent discharge check valve may be connected to the nucleic acid amplifying and detecting device.

The respective chambers may include a nozzle through which air is supplied, and may be disposed to be rotated by a rotating device coupled to the mixing unit so as to be connected with the air pump supplying air to the nozzle.

The nucleic acid amplifying and detecting device may further include a receiving unit, a first heating unit, a second heating unit, a third heating unit, and a rotating unit coupled thereto.

According to a rotation of the rotating unit, the basket may be returned to the receiving unit through the first heating unit, the second heating unit, and the third heating unit.

The first heating unit, the second heating unit, and the third heating unit may be connected to a temperature regulating device, respectively. The temperature of the first heating unit may be maintained to be within a range of about 90° C. to 95° C., the temperature of the second heating unit may be maintained to be within a range of about 40° C. to 65° C., and the temperature of the third heating unit may be maintained to be within a range of about 68° C. to 75° C.

The apparatus may further include an optical device analyzing the nucleic acid amplified by the nucleic acid amplifying and detecting device.

According to an embodiment of the present invention, the apparatus for automatically analyzing a nucleic acid can simplify the process of preprocessing a sample and the process of amplifying and detecting a nucleic acid by the sample preprocessing device and the nucleic acid amplifying and detecting device.

DETAILED DESCRIPTION OF THE EMBODIMENTS

Figure 1:
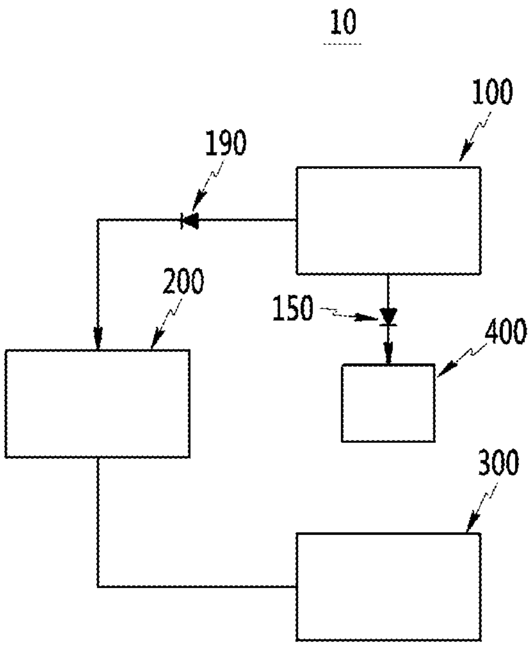
FIG. 1 is a schematic block diagram of an apparatus for automatically analyzing a nucleic acid according to an embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

FIG. 1 is a schematic block diagram of an apparatus for automatically analyzing a nucleic acid according to an embodiment of the present invention.

With reference to FIG. 1, an apparatus 10 for automatically analyzing a nucleic acid according to the present embodiment may include a sample preprocessing device 100, a nucleic acid amplifying and detecting device 200, and an optical device 300 connected to the nucleic amplifying and detecting device 200.

The apparatus 10 for automatically analyzing a nucleic acid according to the present embodiment may further include a residual collecting device 400 connected to the test preprocessing device 100 to collect a residual discharged from the sample preprocessing device 100.

In the present embodiment, the sample preprocessing device 100 may continuously perform a plurality of sample preprocessing processes for extracting a nucleic acid from a sample without time delay and any collateral operation that may be generated between the preprocessing processes.

Here, a nucleic acid may include deoxyribonucleic acid (DNA) and ribonucleic acid (RNA).

However, hereinafter, for the sake of brevity, extracting, amplifying, and detecting DNA by the sample preprocessing device 100 will be described, and a detailed description of RNA will be omitted.

DNA extracted by the sample preprocessing device 100 may be introduced, without being exposed, to the nucleic acid amplifying and detecting device 200 connected to the sample preprocessing device 100 through an effluent discharge check valve 190.

Also, a residual excluding DNA generated in a sample preprocessing process may be discharged to the residual collecting device 400 connected to the sample preprocessing device 100 through a discharge check valve 150.

When the DNA is introduced into the nucleic amplifying and detecting device 200, a plurality of DNA replication processes are successively performed on DNA, without time delay or any collateral operation that may be generated between the replication processes, to replicate DNA.

Also, DNA replicated in the nucleic amplifying and detecting device 200 may be analyzed by an optical device 300 in real time after the respective amplifying and detecting processes are terminated.

Thus, according to the present embodiment, since the plurality of sample preprocessing processes and the DNA replication processes are continuously performed in the sample preprocessing device 100 and the nucleic amplifying and detecting device 200, the processes required for sample preprocessing and DNA replication can be simplified, shortening an overall processing time, preventing the sample from being contaminated, and reducing an unnecessary operation.

Also, according to the present embodiment, since a plurality of processes required for the sample preprocessing and DNA replication are intensively included in each single device, respectively, the structure of the apparatus for automatically analyzing a nucleic acid is simplified.

In addition, according to the present embodiment, a residual that may be generated in the sample preprocessing process is stably collected, preventing an environmental pollution.

Figure 2:
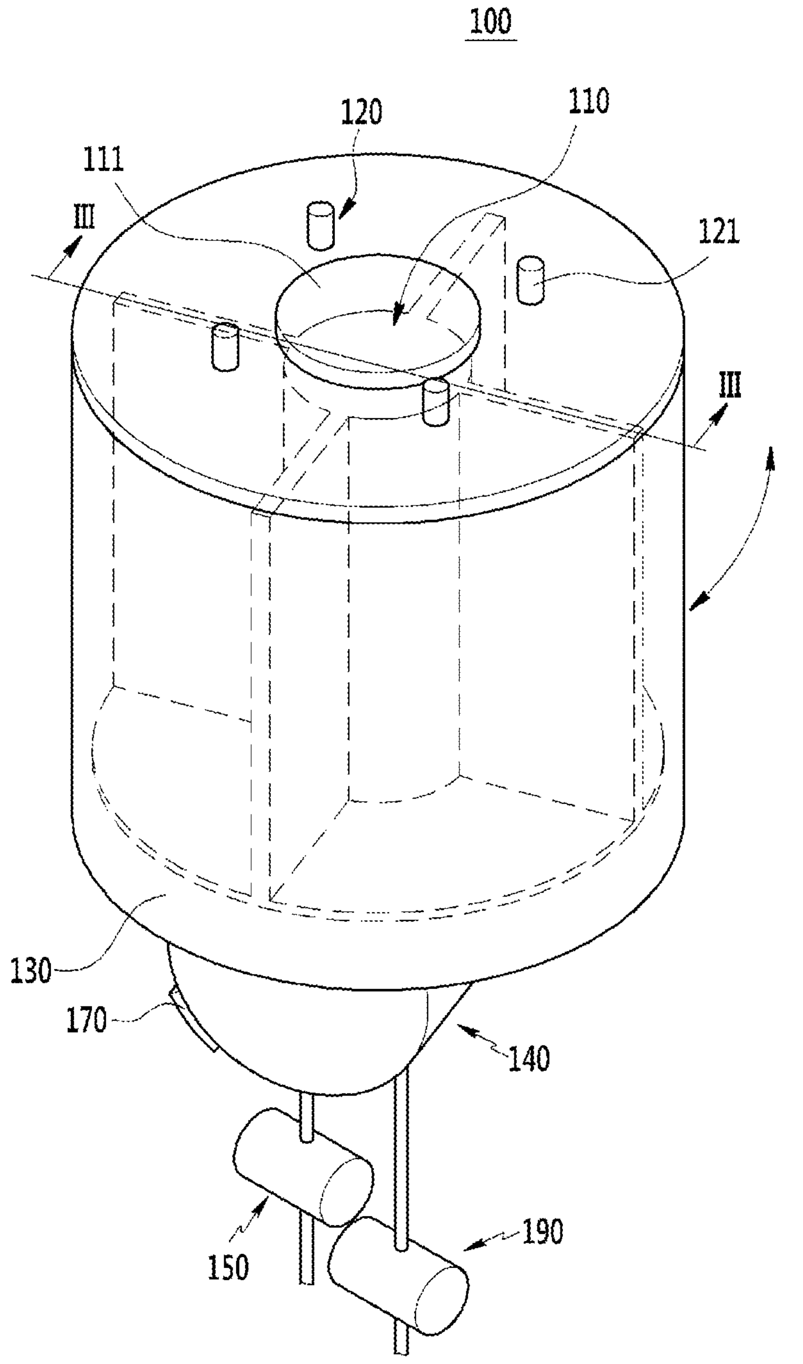
FIG. 2 is a perspective view of a sample preprocessing device according to an embodiment of the present invention.
Figure 3:
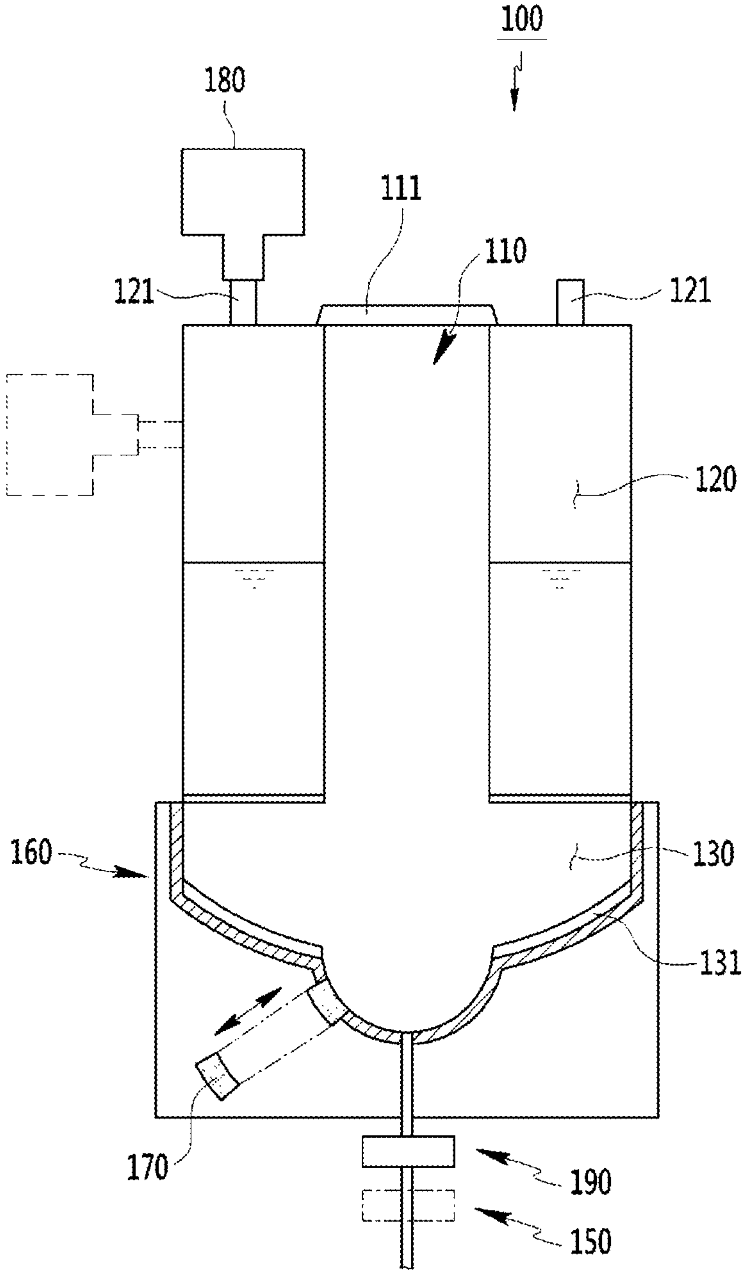
FIG. 3 is a cross-sectional view taken along the line III-III in FIG. 2.
Figure 4:
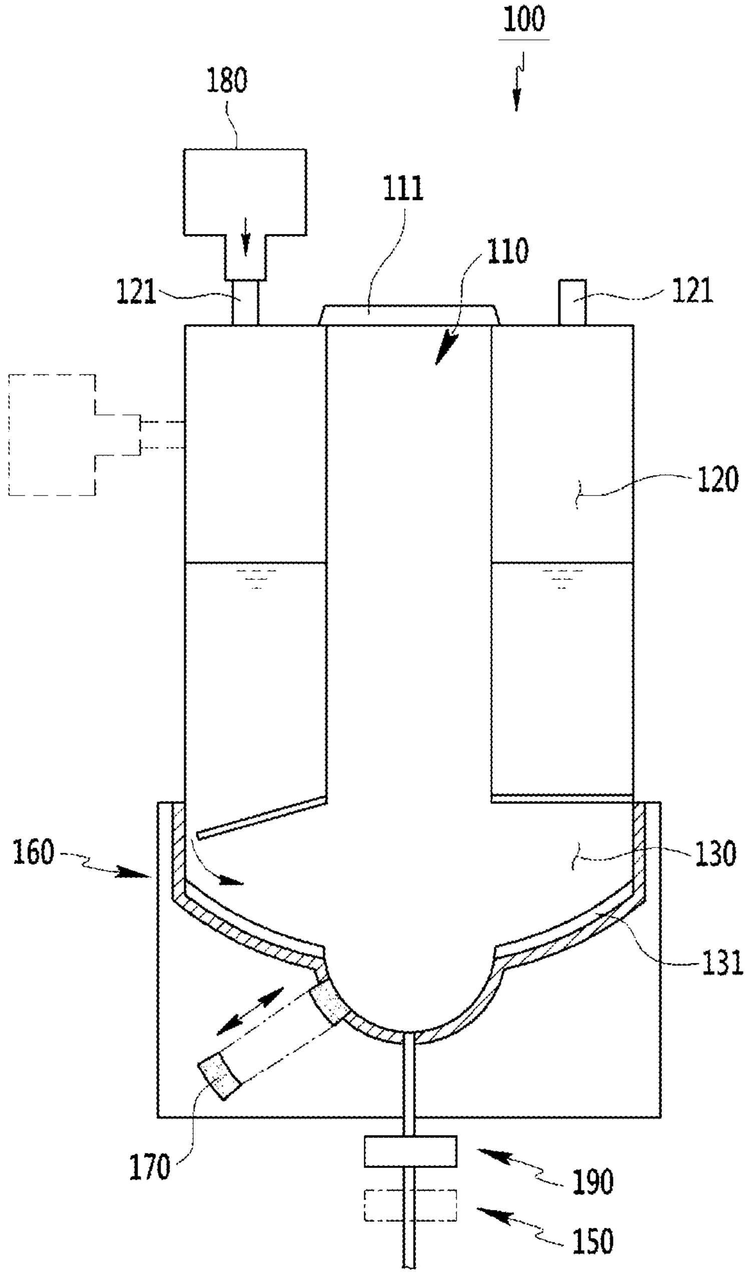
FIG. 4 is a cross-sectional view showing a state in which a chamber of the test preprocessing device of FIG. 3 is pressurized.
Figure 5:
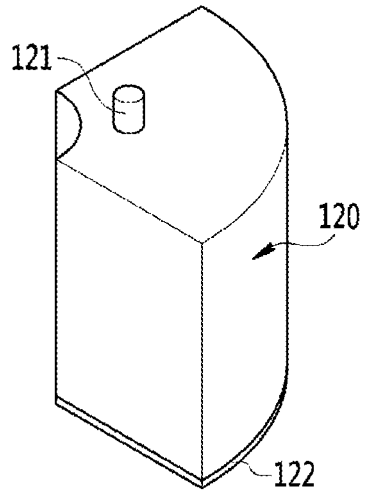
FIG. 5 is a perspective view of a chamber according to an embodiment of the present invention.
Figure 6:
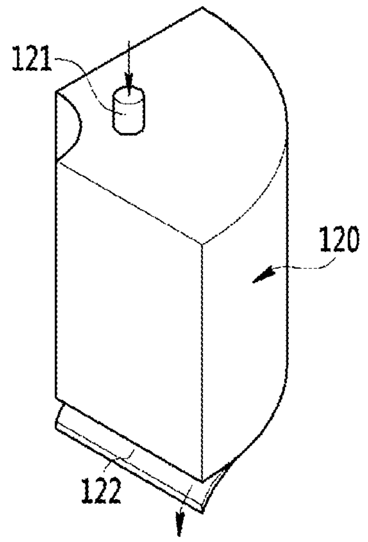
FIG. 6 is a perspective view showing a state in which the interior of the chamber in FIG. 5 is pressurized.

FIG. 2 is a perspective view of a sample preprocessing device according to an embodiment of the present invention. FIG. 3 is a cross-sectional view taken along the line III-III in FIG. 2. FIG. 4 is a cross-sectional view showing a state in which a chamber of the test preprocessing device of FIG. 3 is pressurized. FIG. 5 is a perspective view of a chamber according to an embodiment of the present invention. FIG. 6 is a perspective view showing a state in which the interior of the chamber in FIG. 5 is pressurized.

The sample preprocessing device 100 according to the present embodiment will now be described with reference to FIGS. 2 to 4. The sample preprocessing device 100 according to the present embodiment may include an inlet pipe 110 through a sample is introduced, a plurality of chambers 120, a mixing unit 130 including a baffle, a collecting unit 140, and a magnet bar 170.

According to the present embodiment, the inlet pipe 110 may be coupled to a sample inlet hole (not shown) formed at an upper portion of the mixing unit 130 and have a tubular shape with a hollow portion through which a sample is introduced.

A cover 111 may be installed at the entrance of the inlet pipe 110 such that it opens and closes the entrance to thus prevent a foreign material other than a sample from being introduced into the inlet pipe 110.

Also, the mixing unit 130 may include a sample inlet hole (not shown) through which a sample which has been introduced through the inlet pipe 110 passes, a reagent inlet hole (not shown) through which a reagent is introduced, and a discharge hole (not shown) through which preprocessed sample is discharged. The mixing unit 130 may include a hemispherical case with a hollow portion formed therein.

The chamber 120 may have a substantially hexahedral shape with a hollow portion therein, and a lower portion of the chamber 120 may be installed to oppose an upper portion of the mixing unit 130, and one concave surface of the chamber 120 may be tightly coupled to an outer surface of the inlet pipe 110.

Here, according to the present embodiment, four chambers 120 are installed to be contiguous along the outer surface of the inlet pipe 110 to form a cylindrical shape.

However, the number of the chambers 120 is not limited to four; namely, one or three or less, or five or more chambers may be used according to types of samples, or the like.

One of the pluralities of chambers 120 may be installed such that a lower portion thereof faces a reagent inlet hole (not shown) formed on the mixing unit 130.

Thus, when a lower portion of the chamber 120 is opened, the reagent accommodated in the chamber 120 can be introduced into the mixing unit 130.

For example, one or more reagents among lysis, a solvent (washing solution), an elution buffer, proteinase K, internal control, primer/probe, and enzyme mix may be accommodated in the respective chambers 120.

Opening of the lower portion of the chamber 120 according to the present embodiment of the present invention will be described in detail with reference to FIGS. 3 to 6. A nozzle 121 allowing air to be supplied therethrough may be installed on an upper portion of the chamber 120.

An elastic film 122 may be installed on an opening of the lower portion of the chamber 120. The elastic film 122 according to the present embedment may be configured as an elastic film having a predetermined thickness or may be made to include elastic plastic.

Here, one side of the elastic film 122 is fixed to the lower portion of the chamber 120, so it does not move, and the other side of the elastic film 122 is tightly attached to the lower portion of the chamber 120 but not fixed. Thus the other side of the elastic film 122 may elongate to open a portion of the lower portion of the chamber 120.

For example, as shown in FIG. 6, when air supplied from an air pump 180 connected to the nozzle 121 of the chamber 120 is introduced into the chamber 120 through the nozzle 121 to increase the internal pressure of the chamber 120, the other side of the elastic film 122 installed on the lower portion of the chamber 120 elongates to open a portion of the lower portion of the chamber 120 to allow the reagent accommodated in the chamber 120 to be introduced into the mixing unit 130.

Here, when an amount of reagent required for preprocessing a sample is introduced into the mixing unit 130, air supply into the chamber 120 through the nozzle 121 is stopped, lowering the internal pressure of the chamber 120, and accordingly, the other side of the elastic film 122 elongates to be tightly positioned to the lower portion of the chamber 120, thus closing the lower portion of the chamber 120.

Thus, according to the present embodiment, the amount of reagent introduced into the mixing unit 130 may be regulated according to an opening time of the elastic film 122 over an air supply time duration in which air is supplied to the chamber 120.

Thus, the sample introduced into the mixing unit 130 through the inlet pipe 110 and the reagent introduced into the mixing unit 130 as the lower portion of the chamber 120 is opened can be mixed.

Here, a rotating device 160 may be coupled to the mixing unit 130. Also, since a flow of an effluent of the sample and reagent is irregular in the mixing unit 130 by the baffle 131 installed on the bottom of the mixing unit 130, the sample and the reagent can be mixed within a short time.

Also, the rotating device 160 may rotate the inlet pipe 110 coupled to the mixing unit 130 and the chamber 120 coupled to the outer surface of the inlet pipe 110 only at a certain angle.

For example, as shown in FIGS. 2 and 3, the rotating device 160 may rotate the chamber 120 clockwise or counterclockwise by approximately 90 degrees to move the nozzle 121 of the chamber 120 to a position at which the nozzle 121 can be coupled to the air pump 180.

Thus, the lower portion of the chamber 120 which has been moved by the rotating device 160 is opened by the internal pressure of the chamber 120 increased by the air supplied from the air pump 180, so the reagent required for preprocessing the sample can be discharged into the mixing unit 130.

Thus, according to the present embodiment, the chamber 120 in which reagents required for preprocessing a sample are accommodated is rotated by the rotating device 160 according to sample preprocessing process order to automatically discharge the reagents into the mixing unit 130 by the air pump 180.

Here, the rotating device 160 may use a servomotor as a power source.

Also, the collecting unit 140 according to the present embodiment may be coupled to a portion where a discharge hole of the mixing unit 130 is formed, to collect the effluent of the sample and the reagent mixed in the mixing unit 130.

Here, the effluent may include DNA extracted from the sample preprocessed by the reagent.

A magnet bar 170 may be installed on an outer surface of the collecting unit 140 to collect DNA extracted from the preprocessed sample at an inner side of the collecting unit 140

Also, below the collecting unit 140, there may be installed a residual discharge check valve 150 to discharge a residual, and an effluent discharge check valve 190 to discharge an effluent finally collected from the sample preprocessing process. Here, the effluent discharge check valve 190 may be connected to the nucleic acid amplifying and detecting device 200.

Here, as shown in FIGS. 3 and 4, when a residual is discharged to the outside through the check valve, the magnet bar 170 according to the present embodiment is tightly attached to the outer surface of the collecting unit 140 to collect nucleic acid, and when the residual discharging is completed, the magnet bar 170 may be separated from the outer surface of the collecting unit 140.

Figure 7:
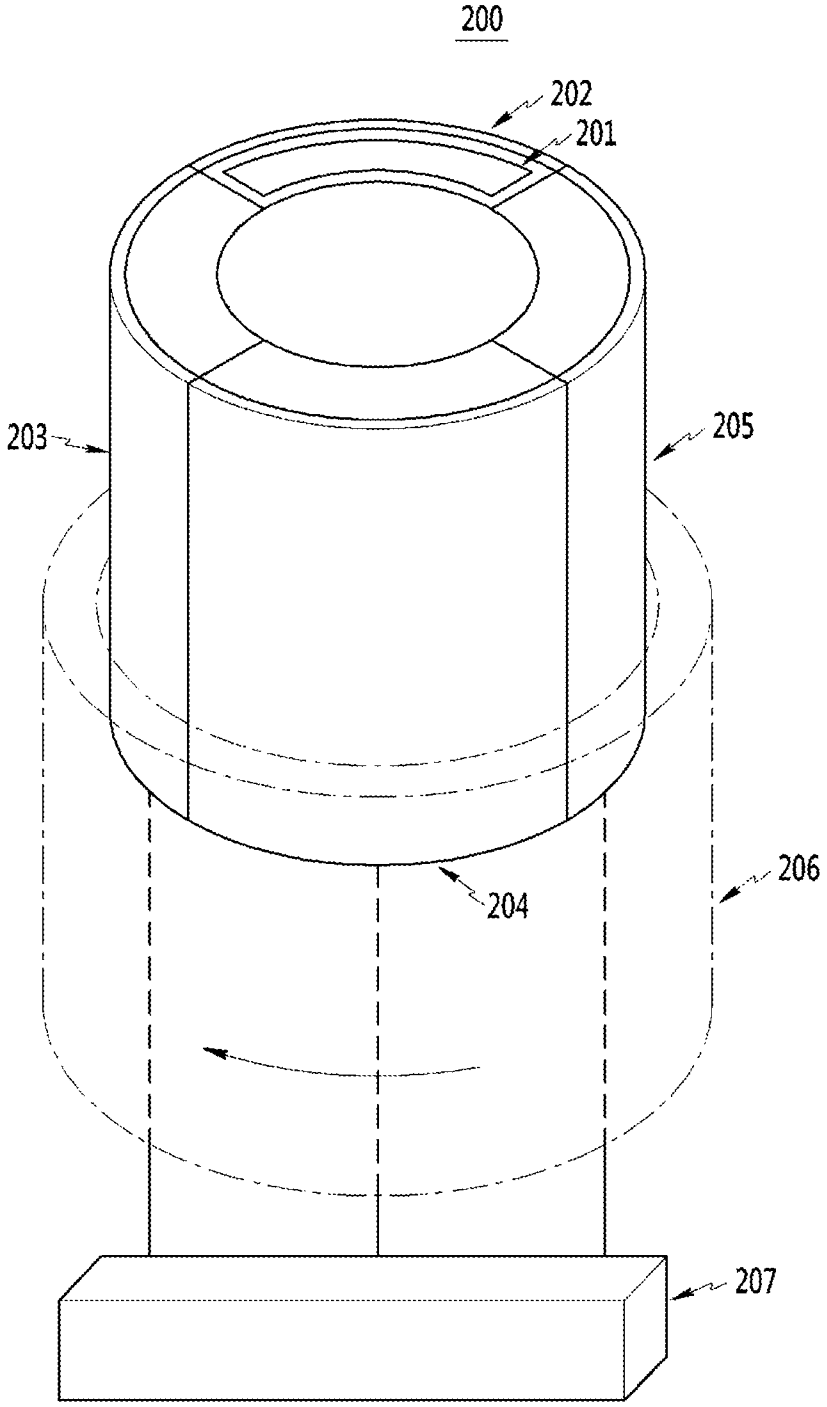
FIG. 7 is a schematic perspective view of a nucleic amplifying and detecting device according to an embodiment of the present invention.
Figure 8:
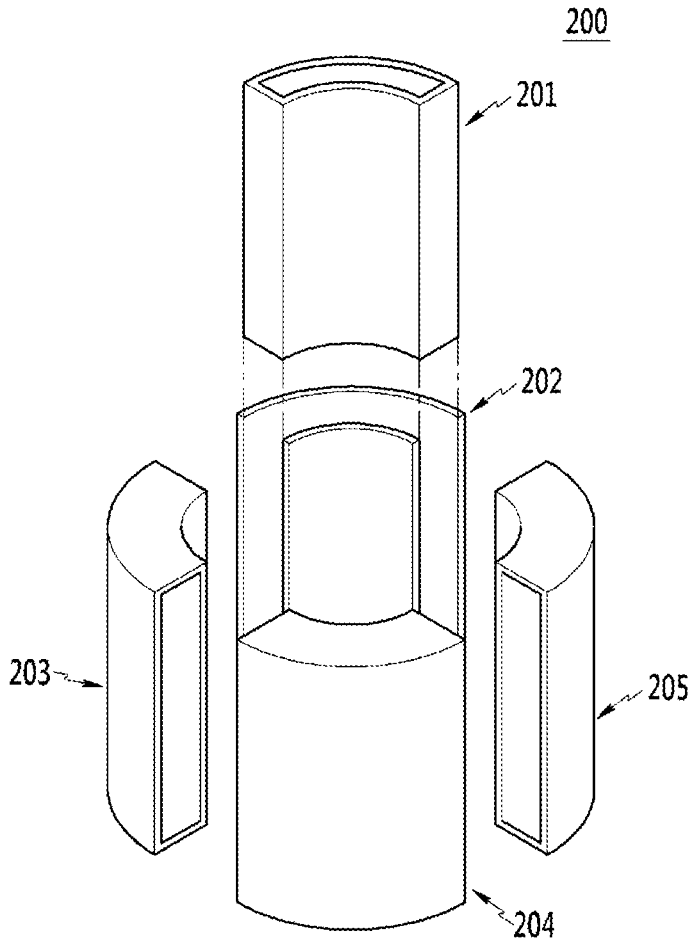
FIG. 8 is an exploded perspective view of the nucleic amplifying and detecting device of FIG. 7.

FIG. 7 is a schematic perspective view of a nucleic amplifying and detecting device according to an embodiment of the present invention. FIG. 8 is an exploded perspective view of the nucleic amplifying and detecting device of FIG. 7.

With reference to FIGS. 7 and 8, the nucleic amplifying and detecting device 200 according to the present invention may include a basket 201 to which DNA extracted from the sample preprocessing device 100 is introduced, a receiving unit 202 accommodating the basket 201, a first heating unit 203, a second heating unit 204, and a third heating unit 205.

The basket 201 according to the present embodiment may have a hexahedral shape having a hollow portion and an opening formed at one side thereof and made of a material having high heat conductivity.

Also, an opening is formed at an upper portion of the receiving unit 202 to allow the basket 201 to be inserted thereinto, and both sides, which are narrow and are in contact with the upper portion of the receiving unit 202, may be open.

Thus, as shown in FIG. 8, the receiving unit 202 may be configured to include outer walls and inner walls which face each other and a lower face connecting the outer walls and the inner walls.

Also, the first heating unit 203 to the third heating unit 205 have a hexahedral shape with a hollow portion formed therein, having a structure in which the sides installed corresponding to the both open narrow sides are opened. The first heating unit 203 to the third heating unit may be made of a material having excellent heat conductivity.

Thus, the first heating unit 203 to the third heating unit 205 according to the present embodiment may be configured to include outer walls and inner walls which face each other and upper lower faces connecting the outer walls and the inner walls.

According to the present embodiment, the receiving unit 202 may be connected to the first heating unit 203, the first heating unit 203 may be connected to the second heating unit 204, the second heating unit 204 may be connected to the third heating unit 205, and the third heating unit 205 may be connected to the receiving unit 202.

Here, the receiving unit 202 and the first heating unit 203 to the third heating unit 205 may be connected to form a cylinder with a hollow portion formed therein, and the residual collecting device 400 may be installed at the lower end of the hollow portion of the cylinder to collect a residual discharged from the sample preprocessing device 100.

Also, an opening is formed at respective sides to which the receiving unit 202 and the first heating unit 203 to the third heating unit 205 are connected, and the respective hollow portions of the receiving unit 202 and the first heating unit 203 to the third heating unit 205 may be connected to form a passage allowing the basket 201 to move therein.

Also, according to the present embodiment, the nucleic acid amplifying and detecting device 200 may further include a rotating unit 206 coupled to the outer face of the cylinder formed as the receiving unit 202, the first heating unit 203, the second heating unit 204, and the third heating unit 205 are coupled. Here, the rotating unit 206 may use the same servo motor, which is used to rotate the rotating device 160 of the sample preprocessing device 100, as a power source.

Thus, with the basket 201 fixed, when the rotating unit 206 rotates at a certain angle (e.g., approximately 90 degrees in the present embodiment), the basket 201 may move to the first heating unit 203.

Also, the basket 201 may move to the second heating unit 204 and the third heating unit 205 by the rotating unit 206, and then, may be returned to the receiving unit 202, for which the nucleic acid amplifying and detecting device 200 may be rotated one time.

The nucleic acid amplifying and detecting device 200 according to the present embodiment may further include a temperature regulating device 207. Here, the temperature regulating device 207 may be connected with the first heating unit 203, the second heating unit 204, and the third heating unit 205, respectively.

Accordingly, the first heating unit 203 may be maintained within a temperature range of 90° C. to 95° C., the second heating unit 204 may be maintained within a temperature range of 40° C. to 65° C., and the third heating unit 205 may be maintained within a temperature range of 68° C. to 75° C., Also, although not described in detail, in the present embodiment, when a ribonucleic acid requiring a reverse-transcription process is used, the receiving unit or the heating unit may be controlled and maintained at a temperature (e.g., 50° C.) required to the reverse-transcription process.

Here, the temperature regulating device 207 according to the present embodiment may include a heating unit (not shown) (e.g., a heating device) and a cooling unit (not shown) (e.g., a cooling fan), and may be installed at the side or at the lower end portion of the nucleic acid amplifying and detecting device 200.

Hereinafter, a polymerase chain reaction (PCR) by the nucleic acid amplifying and detecting device 200 will be described in detail based on the case of an effluent including DNA.

The basket 201 in which the DNA extracted from the sample preprocessing device 100 is accommodated is moved to the first heating unit 203 by the rotating unit 206 and the DNA is heated at a temperature range of about 90° C. to 95° C.

Thus, the DNA is denatured in the first heating unit 203 so as to be separated into double-strand DNA to make each strand.

Also, when the basket 201 is moved from the first heating unit 203 to the second heating unit 204 by an operation of the rotating unit 206, the two separated uni-strand DNAs are cooled at a temperature ranging from about 40° C. to 65° C. so as to be annealed.

Here, in the annealing performing in the second heating unit 204, a primer (a gene sequence of a short single line corresponding to a particular gene sequence and synthesized for the purpose of being used in PCR diagnosis, a DNA base sequence determination method, or the like) may be coupled to a base sequence desired to be amplified in the separated DNA.

Also, when the annealing operation in the second heating unit is terminated, the basket 201 may be rotated to the third heating unit 205 by the rotating unit 206.

Herein the third heating unit 205 may be maintained at a temperature ranging from about 68° C. to 75° C., and a polymerization process (extension) of the DNA may be executed.

Accordingly, when the basket 201 is returned to the receiving unit 202 after passing through the first heating unit 203, the second heating unit 204, and the third heating unit 205 from the receiving unit 202, DNA may be denatured, annealed, and extended in each of the first, second, and third heating units 203, 204, and 205.

Here, in order to complete the processes of denaturing, annealing, and extension, the nucleic acid amplifying and detecting device 200 must be rotated one time.

For example, when it is assumed that denaturing, annealing, and extension processes must be performed 30 times, respectively, in order to complete the PCR in the present embodiment, the nucleic acid amplifying and detecting device 200 must be rotated 30 times.

Figure 9:
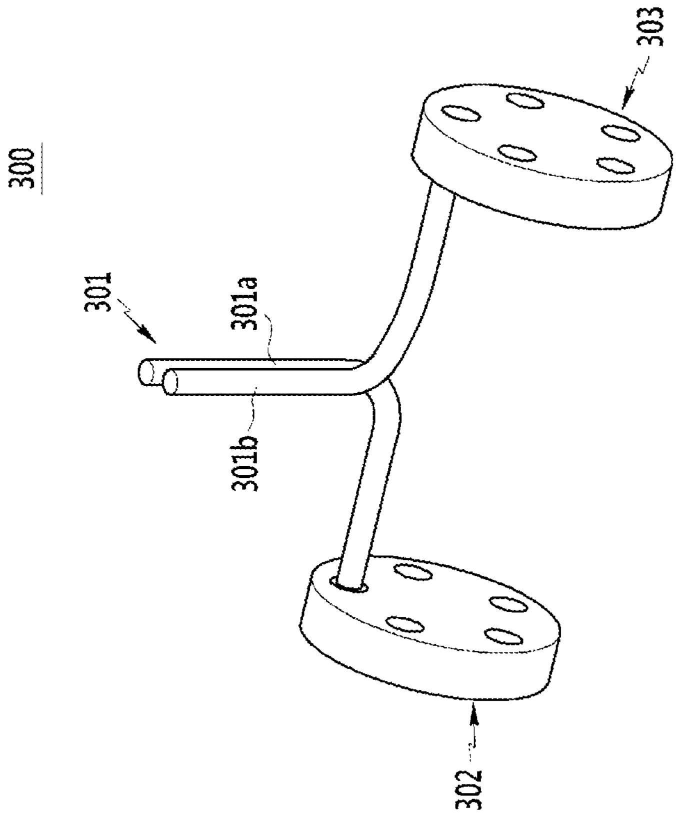
FIG. 9 is a schematic perspective view of an optical device according to an embodiment of the present invention.

FIG. 9 is a schematic perspective view of an optical device according to an embodiment of the present invention. An optical device 300 may be positioned at a lower end or at a side of the third heating unit 205 of the nucleic acid amplifying and detecting device 200.

With reference to FIG. 9, the optical device 300 according to the present embodiment may include a coaxial optical cable 301 including an excitation cable 301*a* and an emission cable 301*b*, or any separate optical cable 301, an excitation filter 302, and an emission filter 303. As a typical excitation light source, an LED, a halogen lamp, and a laser lamp may be used, and in order to detect emission, a photomultiplier tube (PMT), CCD, photodiodes, or the like, may be used.

After the extension process is completed in each cycle, the optical device 300 may detect a nucleic acid in real time and transmit data to an interpretation device, so that the data can be used for an analysis and diagnosis.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

<Description of symbols>

| | |
|---|---|
| 100: sample preprocessing device | 110: inlet pipe |
| 120: chamber | 121: nozzle |
| 130: mixing unit | |
| 131: baffle | |
| 140: collecting unit | |
| 150: residual discharge check valve | |
| 160: rotating device | |
| 170: magnet bar | |
| 190: effluent discharge check valve | |
| 200: nucleic amplifying and detecting device | |
| 201: basket | |
| 202: receiving unit | |
| 203: first heating unit | |
| 204: second heating unit | |

-continued

<Description of symbols>

| |
|---|
| 205: third heating unit |
| 206: rotating unit |
| 207: temperature regulating device |
| 300: optical device |
| 400: Residual collecting device |

What is claimed is:

1. An apparatus for automatically analyzing a nucleic acid, the apparatus comprising:

a sample preprocessing device including a plurality of chambers in which reagents to be mixed with a sample are accommodated according to sample preprocessing process order for extracting a nucleic acid from the sample;

a mixing unit directly coupled to a lower portion of each of the plurality of chambers, receiving a reagent discharged from an opened lower portion of each of the plurality of chambers, and mixing the reagent and the sample, wherein the mixing unit comprises an inlet pipe through which the sample is introduced and the plurality of chambers are directly coupled to an outer surface of the inlet pipe; and a nucleic acid amplifying and detecting device connected with the sample preprocessing device to receive the nucleic acid extracted from the sample.

2. The apparatus of claim 1, wherein the mixing unit comprises a baffle installed on the bottom thereof.

3. The apparatus of claim 1, wherein the chamber comprises a nozzle through which air is supplied, and the lower portion of the chamber is opened and closed according to a change in an internal pressure of the chamber by air supplied through the nozzle.

4. The apparatus of claim 3, wherein an elastic film is installed on an opening formed at a lower portion of the chamber, and when the internal pressure of the chamber is increased by air supplied through the nozzle, the elastic film elongates to open the lower portion of the chamber.

5. The apparatus of claim 4, wherein the elastic film is made of one of an elastic film or elastic plastic.

6. The apparatus of claim 1, wherein the sample preprocessing device further comprises a collecting unit coupled to a lower portion of the mixing unit and collecting an effluent in which the sample and the reagent are mixed.

7. The apparatus of claim 6, wherein the sample preprocessing device further comprises a magnet bar coupled to one side of the collecting unit and collecting DNA extracted from the sample.

8. The apparatus of claim 6, wherein the sample preprocessing device further comprises a residual discharge check valve coupled to a lower portion of the collecting unit to allow a residual to be discharged therethrough; and an effluent discharge check valve allowing the effluent finally collected from the sample preprocessing process to be discharged therethrough, wherein the effluent discharge check valve is connected to the nucleic acid amplifying and detecting device.

9. The apparatus of claim 7, wherein the sample preprocessing device further comprises a rotating device coupled to the mixing unit.

10. The apparatus of claim 6, wherein the respective chambers comprise a nozzle through which air is supplied, and are disposed to be rotated by a rotating device coupled to the mixing unit so as to be connected with the air pump supplying air to the nozzle.

11. The apparatus of claim 1, wherein the nucleic acid amplifying and detecting device comprises:

a basket to which the nucleic acid is introduced, a receiving unit in which the basket is accommodated therein, a first heating unit connected to the receiving unit, a second heating unit connected to the first heating unit, and a third heating unit connected to the second heating unit and the receiving unit, respectively.

12. The apparatus of claim 11, wherein the nucleic acid amplifying and detecting device further comprises:

a rotating unit coupled to the receiving unit, the first heating unit, the second heating unit, and the third heating unit.

13. The apparatus of claim 12, wherein the basket is returned to the receiving unit through the first heating unit, the second heating unit, and the third heating unit according to a rotation of the rotating unit.

14. The apparatus of claim 12, wherein the first heating unit, the second heating unit, and the third heating unit are connected to a temperature regulating device, respectively, the temperature of the first heating unit is maintained to be within a range of about 90° C. to 95° C., the temperature of the second heating unit is maintained to be within a range of about 40° C. to 65° C., and the temperature of the third heating unit is maintained to be within a range of about 68° C. to 75° C.

15. The apparatus of claim 11, further comprising:

an optical device connected to the nucleic acid amplifying and detecting device and analyzing the nucleic acid amplified by the nucleic acid amplifying and detecting device, upon reception.

* * * * *